US011517726B2

(12) United States Patent
Siess et al.

(10) Patent No.: US 11,517,726 B2
(45) Date of Patent: Dec. 6, 2022

(54) INTRAVASCULAR BLOOD PUMP WITH BALLOON

(71) Applicant: Abiomed Europe GMBH, Aachen (DE)

(72) Inventors: Thorsten Siess, Aachen (DE); Christoph Nix, Aachen (DE); Walid Aboulhosn, Aachen (DE)

(73) Assignee: Abiomed Europe GMBH, Aachen (DE)

( * ) Notice: Subject to any disclaimer, the term of this patent is extended or adjusted under 35 U.S.C. 154(b) by 370 days.

(21) Appl. No.: 16/610,773

(22) PCT Filed: May 3, 2018

(86) PCT No.: PCT/EP2018/061350
§ 371 (c)(1),
(2) Date: Nov. 4, 2019

(87) PCT Pub. No.: WO2018/202776
PCT Pub. Date: Nov. 8, 2018

(65) Prior Publication Data
US 2020/0155743 A1  May 21, 2020

(30) Foreign Application Priority Data
May 4, 2017  (EP) ..................................... 17169581

(51) Int. Cl.
*A61M 25/10*  (2013.01)
*A61M 60/13*  (2021.01)
(Continued)

(52) U.S. Cl.
CPC ........ *A61M 25/1002* (2013.01); *A61M 60/13* (2021.01); *A61M 60/135* (2021.01);
(Continued)

(58) Field of Classification Search
CPC ............ A61B 5/02055; A61M 60/414; A61M 60/148; A61M 60/205; A61M 2210/12;
(Continued)

(56) References Cited

U.S. PATENT DOCUMENTS

2019/0175807 A1* 6/2019 Schwammenthal ........................
A61B 5/02055

FOREIGN PATENT DOCUMENTS

EP  3117846 A1  1/2017
EP  3120880 A1  1/2017
(Continued)

OTHER PUBLICATIONS

International Search Report and Written Opinion for Application No. PCT/EP018/061350 dated Jun. 25, 2018.
(Continued)

*Primary Examiner* — Jon Eric C Morales
(74) *Attorney, Agent, or Firm* — Botos Churchill IP Law LLP

(57) ABSTRACT

An intravascular blood pump (1) comprises a ring seal (10) that is configured to assume a collapsed configuration and an expanded configuration and configured to contact and seal against an inner wall of the patient's blood vessel when inserted therein in the expanded configuration. A support member (12; 13) is disposed inside the ring seal (10) in order to support the ring seal (10) from the inside, wherein the support member (12; 13) is configured to collapse at least partially when a predetermined pressure difference between a proximal area and a distal area of the blood vessel acting on the ring seal (10) is exceeded.

18 Claims, 4 Drawing Sheets

(51) Int. Cl.
*A61M 60/135* (2021.01)
*A61M 60/896* (2021.01)
*A61M 60/833* (2021.01)
*A61M 60/861* (2021.01)
*A61M 60/237* (2021.01)

(52) U.S. Cl.
CPC ........ *A61M 60/237* (2021.01); *A61M 60/833* (2021.01); *A61M 60/861* (2021.01); *A61M 60/896* (2021.01); *A61M 2025/1052* (2013.01); *A61M 2025/1061* (2013.01); *A61M 2025/1084* (2013.01); *A61M 2205/0266* (2013.01)

(58) Field of Classification Search
CPC .............. A61M 60/422; A61M 60/833; A61M 60/857; A61M 60/896
See application file for complete search history.

(56) References Cited

FOREIGN PATENT DOCUMENTS

| | | |
|---|---|---|
| WO | 2014141284 A2 | 9/2014 |
| WO | 2016207293 A1 | 12/2016 |

OTHER PUBLICATIONS

Office Action in corresponding Indian Patent Application No. 201937041078 dated Feb. 2, 2022, (6 pages).

\* cited by examiner

INTRAVASCULAR BLOOD PUMP WITH BALLOON

CROSS-REFERENCE TO RELATED APPLICATIONS

This application is a United States National Stage filing under 35 U.S. C. § 371 of International Application No. PCT/EP2018/061350, filed May 3, 2018, which claims priority to European Patent Application No. 17169581.0, filed May 4, 2017. The contents of each of each of the foregoing applications are hereby incorporated by reference in their entirety. International Application No. PCT/EP2018/061350 was published under PCT Article 21(2) in English.

BACKGROUND

This invention relates to an intravascular blood pump for percutaneous insertion into a patient's blood vessel. The blood pump may be a right ventricular assist device, i.e. a blood pump for supporting the function of the right ventricle of a patient's heart.

Intravascular blood pumps are used to support the function of a patient's heart, either as a left ventricular assist device (LVAD) or right ventricular assist device (RVAD). An intravascular blood pump typically comprises a catheter and a pumping device attached to the catheter and is inserted into the patient's heart, e.g. through the aorta into the left ventricle or through the vena cava into the right ventricle. The catheter may have an elongate body with a proximal portion and a distal portion and may extend along a longitudinal axis, wherein the pumping device is attached to the catheter typically at the distal portion remote from an operator, such as a surgeon.

A ventricular assist device may be used for treating dysfunction or dysplasia of a patient's heart, such as congenital heart defects. For instance, during the so-called Fontan procedure, a RVAD is inserted into the patient's heart so as to divert the venous blood from the right atrium to the pulmonary arteries, i.e. the non-functional right ventricle is bypassed by the RVAD. Another application for a RVAD is for patients that suffer from failure of the right ventricle, which may be caused e.g. by a therapy that includes a LVAD. A RVAD may be applied in addition to a LVAD in order to relieve the right ventricle from abnormal high pressures, such as up to 25 mmHg, and avoid failure of the right ventricle during treatment of the left ventricle. Normal healthy venous blood pressure may be in the range from about 3 to 5 mmHg.

When used as a RVAD, the pumping device is advanced towards one lobe of the lung through the pulmonary artery by means of the catheter. Since the outflow of the blood pump is directed to the lung, the pressure difference generated by the blood pump is very crucial, in particular compared to a LVAD, which pumps blood from the left ventricle into the aorta. High pressure may cause harm to the vessels of the lung. A normal, healthy pressure in the pulmonary artery would be in the range from about 10 to 25 mmHg, usually about 15 mmHg. A higher pressure in the pulmonary artery, such as 30 to 40 mmHg, or even 70 mmHg up to 100 mmHg, may be found in patients with heart diseases.

SUMMARY OF THE INVENTION

It is an object of the present invention to provide an intravascular blood pump for percutaneous insertion into a patient's blood vessel, which provides protection against a high pressure difference along the blood vessel.

This object is achieved according to the present invention by a blood pump having the features of independent claim 1. Preferred embodiments and further developments of the invention are specified in the claims dependent thereon.

According to the invention, an intravascular blood pump for percutaneous insertion into a patient's blood vessel is provided, which comprises a catheter, a pumping device and a ring seal with a support member disposed inside the ring seal. The pumping device comprises a blood flow inlet, a blood flow outlet and a rotor so as to cause blood to flow from the blood flow inlet to the blood flow outlet. The ring seal is disposed on the pumping device between the blood flow inlet and the blood flow outlet.

The ring seal can assume a collapsed configuration and an expanded configuration and is configured to contact and seal against an inner wall of the patient's blood vessel when inserted therein in the expanded configuration. In this manner, the ring seal separates a proximal area of the blood vessel from a distal area of the blood vessel. The support member is disposed inside the ring seal in order to support the ring seal from the inside, wherein the support member is configured to collapse at least partially when a predetermined pressure difference between the proximal area and the distal area of the blood vessel acts on the ring seal. At the same time, the support member is configured to withstand a pressure difference of up to 100 mmHg, preferably less, such as up to 50 mmHg, preferably up to 20 mmHg. Throughout this disclosure, the term "distal" refers to directions away from a user and towards the heart, whereas the term "proximal" refers to directions towards a user. In other words, the ring seal collapses when the pressure difference that is created by the blood pump between an inlet side and an outlet side is greater than the predetermined value. Preferably, the blood pump is configured to be inserted into a pulmonary artery.

The support member is particularly a mechanical support member as described in more detail below. While the support member is configured to keep the ring seal in the expanded configuration up to a predetermined pressure difference, it is at the same time flexible enough to ensure that the predetermined pressure difference between the proximal and distal areas in the blood vessel is not exceeded. This is important to limit the pressure increase that is created for example by a blood pump in a pulmonary artery. The ring seal does not occlude the blood vessel at a pressure difference of 100 mmHg or more, preferably 20 mmHg or more as described in more detail below. In other words, the ring seal acts like an overpressure valve, which means that blood is allowed to flow in a direction towards the lower pressure side past the ring seal once a predetermined threshold for the pressure difference is exceeded. The provision of the ring seal, thus, provides a self-regulating pressure in the blood vessel. An internal pressure of the ring seal is preferably atmospheric, i.e. the interior of the ring seal may be in fluid communication with the environment, e.g. by means of an open line.

The ring seal, in particular its outer general shape independent of the catheter body extending there through, may have any size and shape appropriate for a desired application. For instance, the ring seal may be spherical, ellipsoidal, cylindrical or a combination thereof. The ring seal may be symmetric, in particular axially symmetric, with respect to a central longitudinal axis of the catheter, or asymmetric. An outer diameter of the ring seal, in particular in the expanded configuration, may be chosen dependent on the application.

In one embodiment, which may be suitable for an application in a pulmonary artery, the outer diameter of the ring seal in the expanded configuration may be from about 1 cm to about 2.5 cm. The pumping device may have a length of about 3 to 6 cm.

Preferably, the support member is configured to withstand a predetermined pressure difference between the proximal area and distal area of up to about 20 mmHg, which is an appropriate pressure difference for an application in which the catheter is advanced into a pulmonary artery. In other words, the support member is configured to maintain the expanded configuration of the ring seal at a pressure difference between the proximal area and distal area in the blood vessel up to 20 mmHg, and collapses once the pressure difference exceeds 20 mmHg. Depending on a desired application, the predetermined pressure difference may be in the range from about 5 mmHg to about 35 mmHg, more preferably from about 7 mmHg to about 30 mmHg.

In one embodiment, the ring seal comprises a flexible membrane. In particular, the membrane may be flexible and elastic. In this manner, the membrane is able to follow the expanded and collapsed configuration of the ring seal. The membrane may form a casing that encloses the support structure. In particular, the membrane may form a balloon having an inflation port that allows fluid to be supplied to and to be removed from the balloon. The inflation port may be connected to a fluid line extending along the elongate body of the catheter so as to allow to inflate the balloon by supplying fluid to the balloon and to deflate the balloon by removing fluid from the balloon. In particular, the fluid line may be a vacuum line in order to allow creating a vacuum or negative pressure in the balloon to collapse the ring seal. The balloon and fluid line may be suitable for any fluid, such as liquids or gases, in particular saline or air. As mentioned above, the pressure in the ring seal may be atmospheric pressure. Therefore, the fluid line that is connected to the balloon may be open to the environment or otherwise configured to level the pressure inside the balloon to atmospheric pressure.

The support member may be at least partially compressible. This allows the support member to stay inside the ring seal even in the collapsed configuration. Alternatively, or in addition, the support member may be retracted from the ring seal in order to bring the ring seal from the expanded configuration to the collapsed configuration.

Preferably, the support member is biased to the expanded configuration. This provides the ring seal with self-expanding (or self-inflating) and self-holding characteristics. In other words, no external actuation is needed to bring the ring seal from the collapsed configuration to the expanded configuration because the ring seal tends to assume the expanded configuration when no loads are applied. In particular, while the ring seal may be held in the collapsed configuration by applying a vacuum, releasing the vacuum may cause the ring seal to expand. It will be appreciated that, nevertheless, expansion of the ring seal might be enhanced by external actuation, e.g. by means of a pressurized fluid that is supplied to the ring seal.

In one embodiment, the support member may comprise a foam or sponge. The foam may be a closed-cell foam or an open-cell foam. The foam can assume an expanded configuration e.g. at atmospheric pressure and may be compressed by applying a vacuum or other external force on the ring seal. In particular, if the foam is enclosed by a flexible membrane, the ring seal comprising the foam and the membrane is particularly suitable to adapt to the size and shape of an inner vessel wall. The characteristics of the foam may be chosen to allow the ring seal to collapse at a predetermined minimum pressure. The foam may comprise any suitable material, in particular a polymeric material, such as polyurethane. The structure of the foam or sponge is chosen to set the predetermined minimum pressure at which the ring seal shall collapse, or in other words to set a predetermined pressure difference up to which the support structure maintains the expanded configuration.

In another embodiment, the support member may comprise at least one elastic wire, preferably made of a shape memory material, such as Nitinol. Alternative materials that have shape memory characteristics or superelastic characteristics, such as nylon, can be used. Generally, shape memory is a temperature dependent property that allows the shape memory material the ability to undergo deformation at one temperature and then recover its original, undeformed shape upon heating above its "transformation temperature". The temperature change causes a transformation between the martensite phase and austenite phase of the material. Superelasticity is a temperature independent property that allows the shape memory material the ability to undergo a mechanical deformation due to an external force applied to the shape memory material, and then recover its original undeformed shape upon release of the external force. The superelasticity, which is also referred to as pseudoelasticity, is caused by a transformation between the martensite phase and the austenite phase that occurs due to external loads.

The wire, which may be made of Nitinol as mentioned above, can be retracted from the ring seal in order to be able to collapse the ring seal. Upon retraction of the wire, it can be straightened by pulling it into a lumen of the catheter. Vice versa, when the wire is advanced into the ring seal, it may assume a curved shape to thereby expand the ring seal. The curved shape may be a predetermined shape of the shape memory material, and may be e.g. helical or otherwise shaped to provide a desired expanded configuration of the ring seal. In particular, the wire may apply a force to the flexible membrane from the inside of the ring seal to expand the ring seal. In addition, although not necessary, the ring seal may be filled with a fluid, such as a liquid or gas upon expansion. Accordingly, the fluid may be removed from the ring seal upon retraction of the elastic wire from the ring seal.

In one embodiment, the ring seal may comprise a flexible shield extending from an outer circumference of the ring seal, i.e. an outer circumferential surface of a body portion of the ring seal. The flexible shield may be configured to contact the inner vessel wall when the catheter is inserted in the blood vessel and the ring seal is in the expanded configuration. The shield may be relatively soft and flimsy compared to the body portion of the ring seal, which may reduce the risk of causing harm to the blood vessel and may further improve adaptation of the ring seal to the size and shape of the blood vessel. The shield may be formed as a skirt or sleeve that surrounds the ring seal and is supported by the ring seal. The shield preferably collapses and expands as the ring seal collapses. The shield may have a proximal end attached to the ring seal and a free distal end configured to contact the inner vessel wall. Thus, the shield may be open in a direction of the blood flow in order to prevent a backflow and improve the sealing characteristics. However, since the shield collapses as the ring seal collapses the pressure difference in the blood vessel is limited as described above.

The shield may comprise a stiffening structure. The stiffening structure may have at least one fluid receiving channel configured to be inflated by receiving a fluid in order to stiffen the shield and to be deflated by removing the fluid in order to soften the shield. For example, the shield may have longitudinally extending channels to form an umbrella-like shield. It will be appreciated that any other size, shape, number and configuration of the channels may be possible that is suitable to provide stiffness for the shield, e.g. helically curved. The channel or channels may be completely filled or emptied or only partially filled or emptied. This may allow to adjust the stiffness of the shield.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
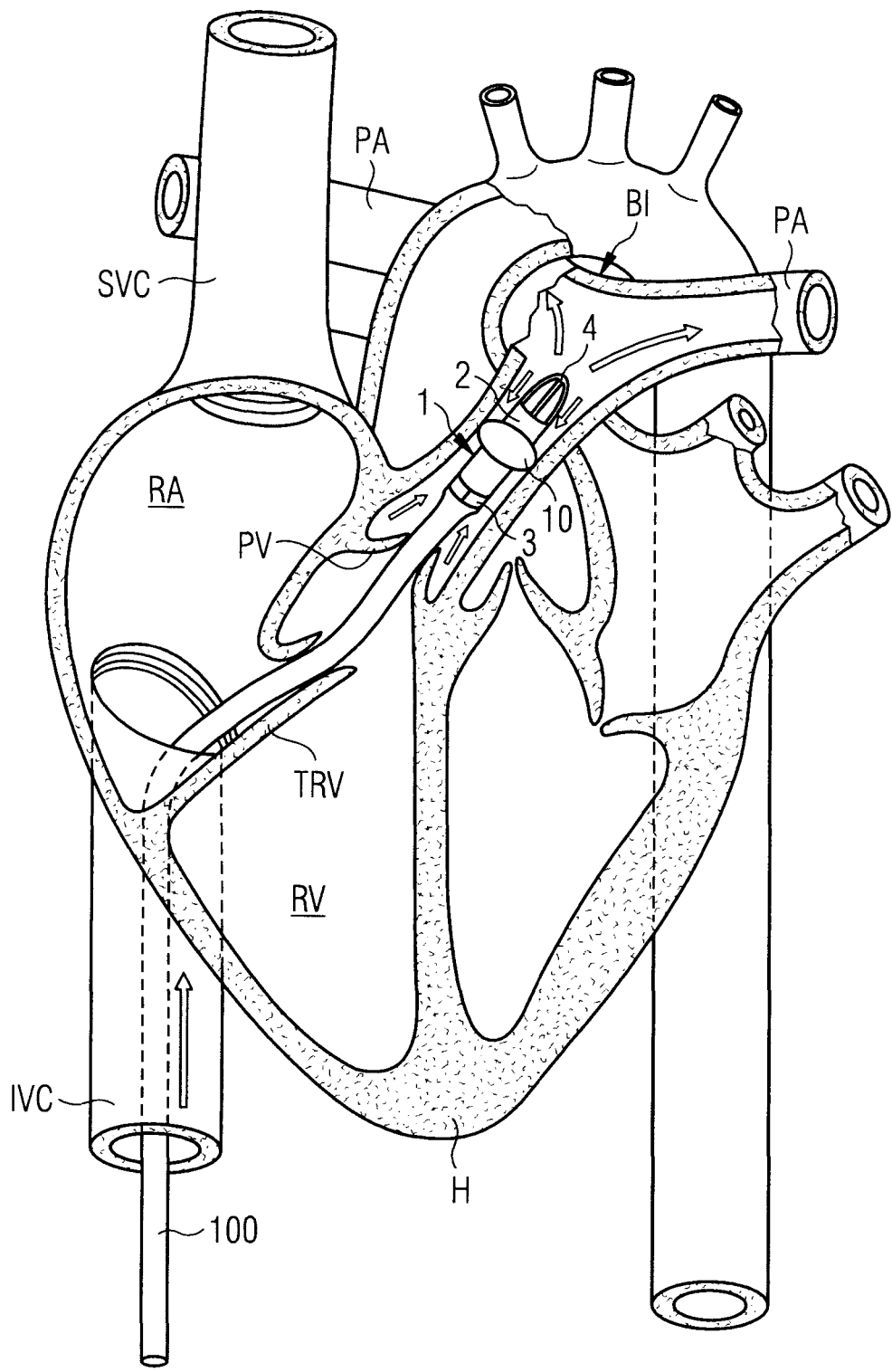
FIG. 1 shows an intravascular blood pump inserted in a patient's heart.

In FIG. 1 is illustrated an intravascular blood pump 1 inserted into a patient's heart H. More specifically, in this illustrative embodiment, the blood pump 1 comprises a catheter 100 by means of which the blood pump 1 is inserted into the pulmonary artery PA through the right ventricle RV of the patient's heart H via the inferior vena cava IVC. In a different approach, the catheter may be inserted through the superior vena cava SVC. During its operation, the blood pump 1, in particular the catheter 100 extends through the tricuspid valve TRV and the pulmonary valve PV. The blood pump 1 comprises a pumping device 2 having a blood flow inlet 3 and a blood flow outlet 4. An impeller or rotor (not shown) is provided to cause the blood to flow into the blood flow inlet 3 towards and out of the blood flow outlet 4. The blood pump 1 according to this embodiment is designed as a right ventricular assist device (RVAD) and may be used e.g. in a Fontan procedure or in addition to a left ventricular assist device (LVAD). The pumping device 2 is placed in the pulmonary artery PA.

The blood pump 1, in particular the pumping device 2, is provided with a ring seal 10. The ring seal 10, which is described in more detail below with reference to FIGS. 2-6 can assume an expanded configuration and a collapsed configuration and is shown in the expanded configuration in FIG. 1. The ring seal 10 contacts the inner wall of the pulmonary artery PA and, thus, seals a proximal portion of the pulmonary artery PA against a distal portion of the pulmonary artery PA. The operation of the blood pump 1 creates a pressure difference between the proximal and distal portions of the pulmonary artery PA, more specifically a pressure increase from the proximal portion towards the distal portion. In order to limit the pressure increase, the ring seal 10 is configured to collapse once a predetermined minimum pressure difference between the proximal and distal portions of the pulmonary artery PA is reached, i.e. the ring seal 10 withstands a pressure difference of up to a predetermined pressure difference. The ring seal 10 in the collapsed configuration allows blood to flow from the distal portion of the pulmonary artery PA towards the proximal portion of the pulmonary artery PA past the pumping device 2. Once the pressure difference falls below the predetermined minimum pressure, the ring seal 10 may expand again. This is promoted by self-expansion properties of a support member inside the ring seal 10 as will be described in more detail below. The predetermined minimum pressure difference may be about 20 mmHg for an application in the pulmonary artery PA.

Figure 2:
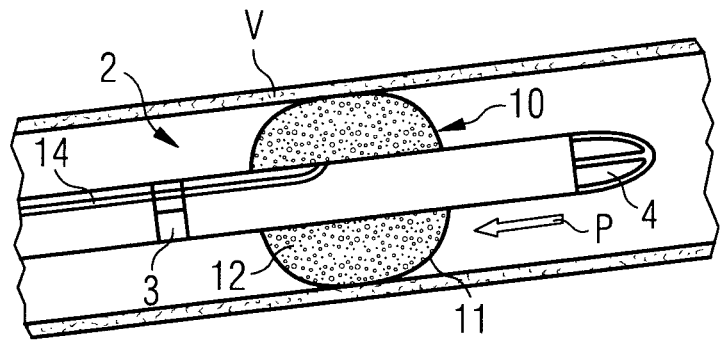
FIG. 2 shows a cross-sectional schematic view of a ring seal of a catheter according to one embodiment in the expanded configuration.

Referring now to FIG. 2, the ring seal 10 of the pumping device 2 is shown in a schematic longitudinal cross-sectional view inserted into a blood vessel V. It will be appreciated that details of the blood pump 1 are omitted for the sake of simplicity. FIG. 2 shows the ring seal 10 in the expanded configuration disposed about the pumping device 2. The ring seal 10 comprises a flexible membrane 11 that forms a balloon-like element. The flexible membrane 11 encloses a support member 12, which comprises a foam in this embodiment, in particular a polyurethane foam. The foam is biased to the expanded configuration to provide self-expanding and self-holding properties for the ring seal 10. Preferably, the interior of the ring seal 10 is under atmospheric pressure, when in the expanded configuration. A vacuum line 14 may be provided to remove fluid, such as a liquid or gas, from the ring seal 10 to bring the ring seal 10 actively into the collapsed configuration, e.g. during insertion of the pumping device 2 or for removal of the pumping device 2 from the patient's heart H.

Figure 3:
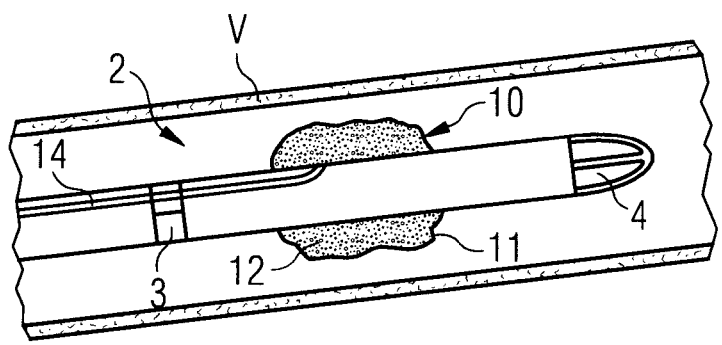
FIG. 3 shows the ring seal of FIG. 2 in the collapsed configuration.

The ring seal 10 is shown in the collapsed configuration in FIG. 3. In the collapsed configuration, the foam is at least partially compressed. This may be achieved by removing fluid from the ring seal 10. In particular, however, the ring seal 10 collapses automatically when a predetermined pressure difference between opposing sides that acts on the ring seal 10 is exceeded. The minimum pressure difference may be between 7 mmHg and 30 mmHg, and may preferably be 20 mmHg. The direction of the pressure difference between a higher pressure and a lower pressure is indicated at arrow P in FIG. 2.

Figure 4:
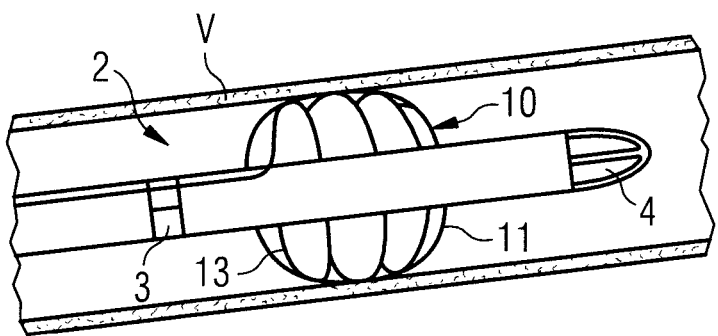
FIG. 4 shows a cross-sectional schematic view of a ring seal of a catheter according to another embodiment in the expanded configuration.
Figure 6A:
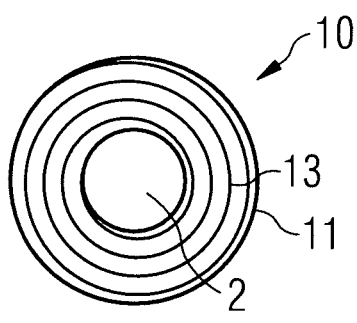
FIGS. 6a and 6b show cross-sectional views of different examples of a ring seal for the embodiment of FIG. 4.
Figure 6B:
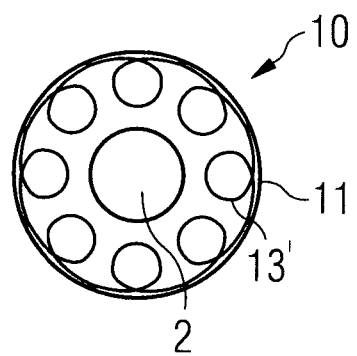

Another embodiment is shown in FIG. 4, which is similar to the embodiment of FIGS. 2 and 3 except for the support member in the ring seal 10. FIG. 4 does not show a vacuum line 14. However, it will be appreciated that a vacuum line may be provided also in this embodiment. The support member 13 comprises an elastic wire, in particular made of a shape memory material, such as Nitinol. The wire is shown schematically in FIG. 4. FIGS. 6a and 6b show different examples for an elastic wire in a cross-sectional view perpendicular to a longitudinal axis of the pumping device 2. In order to expand the ring seal 10, the wire is advanced into the interior of the ring seal 10, e.g. from a lumen that extends along the catheter 100 into the pumping device 2 and that straightens the wire. The wire will assume its predetermined curved shape once advanced into the ring seal 10. The curved shape may be e.g. helical as shown in FIG.

Figure 5:
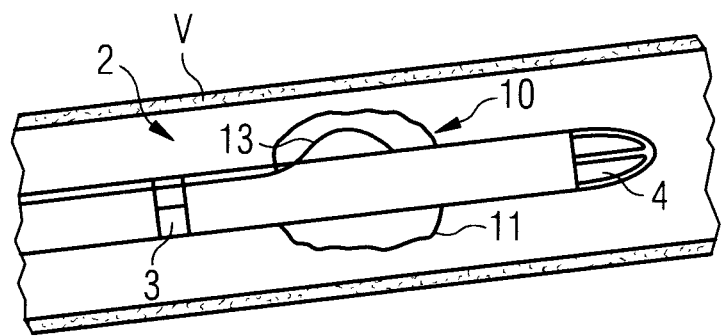
FIG. 5 shows the ring seal of FIG. 4 in the collapsed configuration.

6a or otherwise curved as shown exemplarily in FIG. 6b. The wire acts on the flexible membrane 11 from the interior of the ring seal 10 and, thus, expands the ring seal 10. In order to collapse the ring seal 10, the wire can be retracted from the ring seal 10 as shown in FIG. 5. The wire is configured to allow the ring seal 10 to collapse when a predetermined minimum pressure acts on the ring seal 10, or in other words configured to support the ring seal 10 to withstand a pressure difference only up to a predetermined pressure difference.

Figure 7:
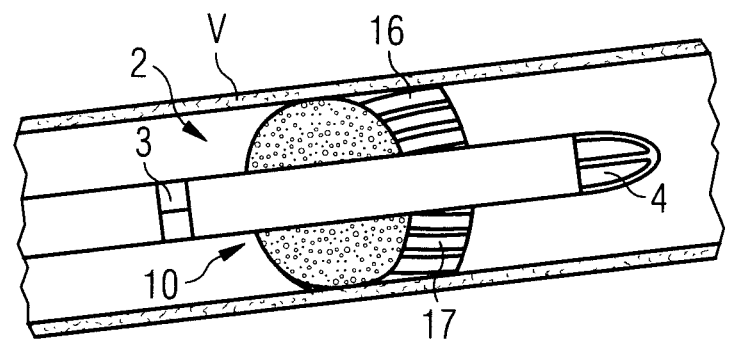
FIG. 7 shows a cross-sectional schematic view of a ring seal of a catheter according to yet another embodiment in the expanded configuration.
Figure 8:
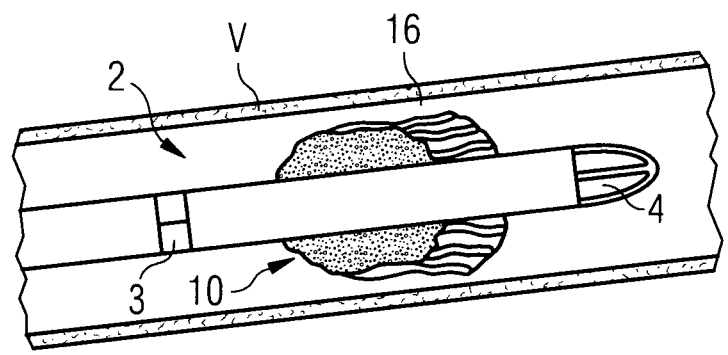
FIG. 8 shows the ring seal of FIG. 7 in the collapsed configuration.

In another embodiment, shown in FIG. 7, the ring seal 10 comprises a flexible shield 16 extending from a body portion of the ring seal 10. The shield 16 is disposed on a circumference of the ring seal 10 and is configured to contact the inner wall of the vessel V when the ring seal 10 is in the expanded configuration as shown in FIG. 7. The shield 16 may comprise a membrane and may be relatively flimsy to protect the vessel wall and to improve sealing against the vessel wall. Channels 17 may be provided as a stiffening structure that may be filled with a fluid to stiffen the shield 16. In order to soften the shield 16, the fluid may be removed from the channels 17. As shown in FIG. 8, the shield 16 collapses together with the ring seal 10 in the collapsed configuration. As in the previous embodiments, the ring seal 10 including the shield 16 is configured to collapse when a predetermined minimum pressure difference between the proximal portion of the pulmonary artery PA and the distal portion of the pulmonary artery PA acts on the ring seal 10 in order to avoid a too high pressure increase in the pulmonary artery PA.

The invention claimed is:

1. An intravascular blood pump for percutaneous insertion into a patient's blood vessel, comprising:
    a catheter,
    a pumping device attached to the catheter, the pumping device having a blood flow inlet, a blood flow outlet and a rotor so as to cause blood to flow from the blood flow inlet to the blood flow outlet,
    a ring seal disposed on the pumping device between the blood flow inlet and the blood flow outlet, the ring seal configured to assume a collapsed configuration and an expanded configuration and configured to contact and seal against an inner wall of the patient's blood vessel when inserted therein in the expanded configuration so as to separate a proximal area of the patient's blood vessel from a distal area of the patient's blood vessel, and
    a support member disposed inside the ring seal in order to support the ring seal from inside the ring seal, wherein the support member is configured to collapse at least partially when a predetermined pressure difference during operation of the intravascular blood pump between the proximal area of the patient's blood vessel and the distal area of the patient's blood vessel acts on the ring seal, wherein the support member withstands a pressure difference during operation of the intravascular blood pump between the proximal area of the patient's blood vessel and the distal area of the patient's blood vessel of up to 100 mmHg before it collapses.

2. The intravascular blood pump of claim 1, wherein the support member is configured to withstand a pressure difference during operation of the intravascular blood pump between the proximal area of the patient's blood vessel and the distal area of the patient's blood vessel of up to 20 mmHg before it collapses.

3. The intravascular blood pump of claim 1, wherein the support member is configured to withstand a pressure difference during operation of the intravascular blood pump between the proximal area of the patient's blood vessel and the distal area of the patient's blood vessel from about 5 mmHg to about 35 mmHg.

4. The intravascular blood pump of claim 1, wherein the ring seal comprises a flexible membrane.

5. The intravascular blood pump of claim 4, wherein the ring seal forms a balloon having an inflation port that allows fluid to be supplied to and to be removed from the balloon.

6. The intravascular blood pump of claim 5, wherein the inflation port is connected to a fluid line so as to allow to inflate the balloon by supplying fluid to the balloon and to deflate the balloon by removing fluid from the balloon.

7. The intravascular blood pump of claim 1, wherein the support member is at least partially compressible.

8. The intravascular blood pump of claim 1, wherein the support member is biased to the expanded configuration.

9. The intravascular blood pump of claim 1, wherein the support member comprises a foam or sponge.

10. The intravascular blood pump of claim 1, wherein the support member comprises at least one elastic wire.

11. The intravascular blood pump of claim 10, wherein the at least one elastic wire is made of a shape memory material.

12. The intravascular blood pump of claim 11, wherein the shape memory material is Nitinol.

13. The intravascular blood pump of claim 1, wherein an outer diameter of the ring seal in the expanded configuration is from about 1 cm to about 2.5 cm.

14. The intravascular blood pump of claim 1, wherein the ring seal comprises a flexible shield extending from an outer circumference of the ring seal, the flexible shield configured to contact the inner wall of the patient's blood vessel when the catheter is inserted in the patient's blood vessel and the ring seal is in the expanded configuration.

15. The intravascular blood pump of claim 14, wherein the flexible shield has a proximal end attached to the ring seal and a free distal end configured to contact the inner wall of the patient's blood vessel.

16. The intravascular blood pump of claim 14, wherein the flexible shield comprises a stiffening structure having at least one fluid receiving channel configured to be inflated by receiving a fluid in order to stiffen the flexible shield and to be deflated by removing the fluid in order to soften the flexible shield.

17. The intravascular blood pump of claim 1, configured to be inserted into a pulmonary artery.

18. The intravascular blood pump of claim 1, wherein the support member is configured to withstand a pressure difference during operation of the intravascular blood pump between the proximal area of the patient's blood vessel and the distal area of the patient's blood vessel from about 7 mmHg to about 30 mmHg.

* * * * *